United States Patent [19]

Nebel et al.

[11] 4,067,025
[45] Jan. 3, 1978

[54] SELF DEVELOPING CAMERA FOR USE IN MACROPHOTOGRAPHY AND ENDOSCOPIC PATHOLOGY

[75] Inventors: Otto T. Nebel, Solana Beach; Louis J. Trujillo; Carl C. Russell, both of San Diego, all of Calif.

[73] Assignee: The United States of America as represented by the Secretary of the Navy, Washington, D.C.

[21] Appl. No.: 682,815

[22] Filed: May 3, 1976

[51] Int. Cl.² .............................................. G03B 15/14
[52] U.S. Cl. ...................................... 354/62; 354/123
[58] Field of Search ................ 354/62, 123, 120, 121, 354/122, 195, 286

[56] References Cited

U.S. PATENT DOCUMENTS

| 1,892,683 | 1/1933 | Robertson | 354/123 X |
| 3,599,630 | 8/1971 | Sato | 354/62 X |
| 3,641,900 | 2/1972 | Ataka et al. | 354/123 |
| 3,741,098 | 6/1973 | Cannon | 354/123 |
| 3,877,043 | 4/1975 | Marvel | 354/123 |
| 3,884,222 | 5/1975 | Moore | 354/62 X |
| 3,918,072 | 11/1975 | Imai et al. | 354/62 |

FOREIGN PATENT DOCUMENTS 609,853  10/1948  United Kingdom ................ 354/286

*Primary Examiner*—Edna M. O'Connor
*Attorney, Agent, or Firm*—Richard S. Sciascia; Ervin F. Johnston; William T. Skeer

[57] ABSTRACT

An endoscopic photographic system includes the body inserted endoscope connected via a fiber optic bundle to a photographic lens carrier in a focusing mount. The photographic lens is provided with a compound sliding mount which positions it on a camera back supporting a self developing film plate in the focal plane of the lens. By moving the compound mount, a plurality of photographs may be obtained on a single self developing plate such that timely diagnosis may be readily facilitated.

5 Claims, 7 Drawing Figures

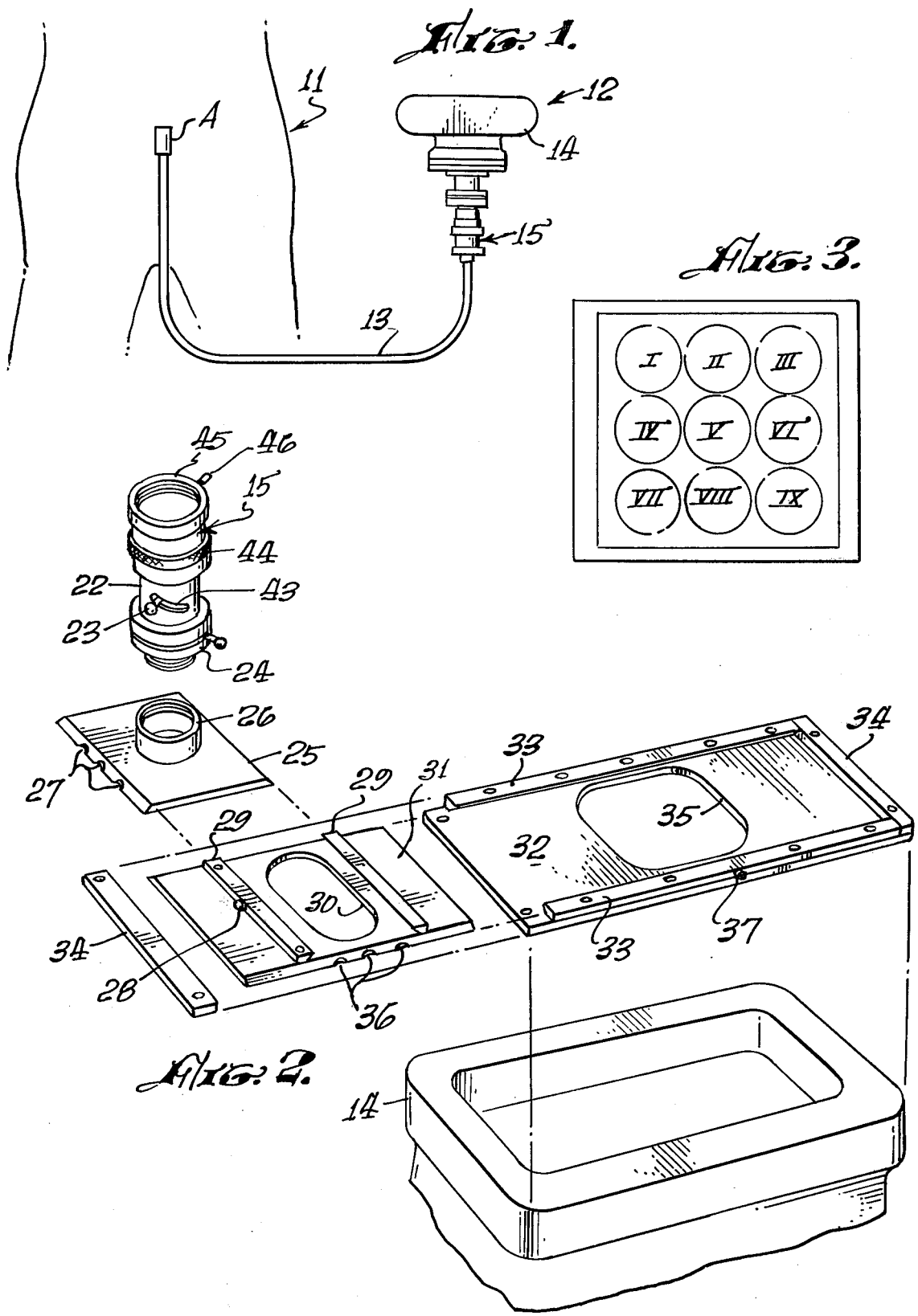

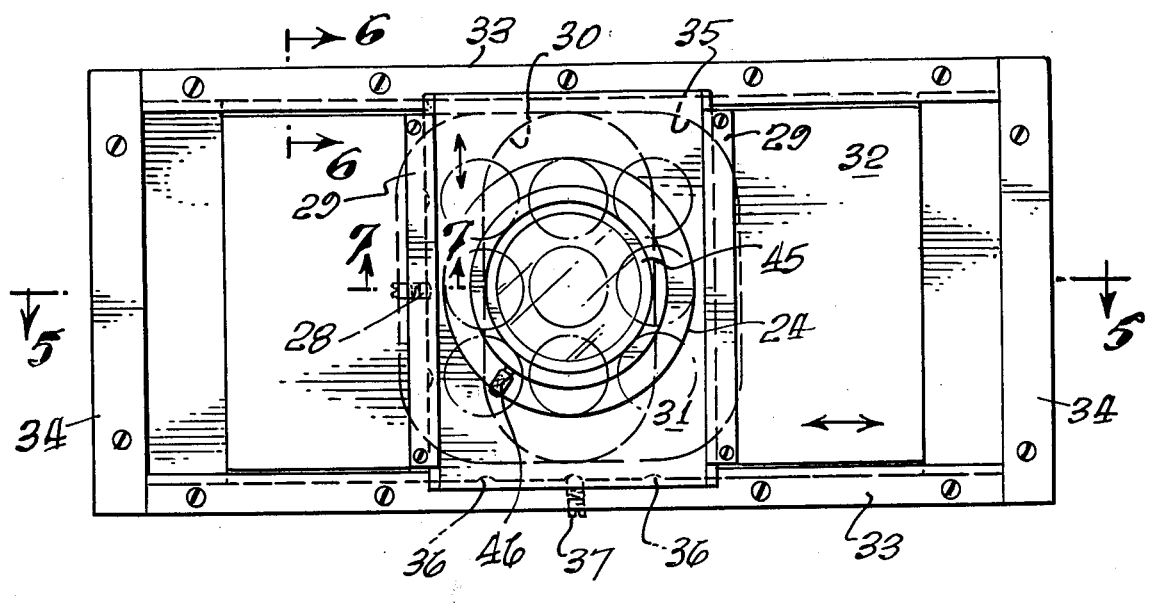
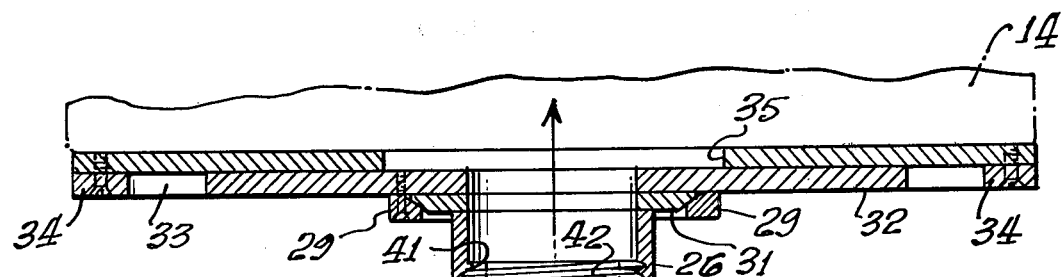
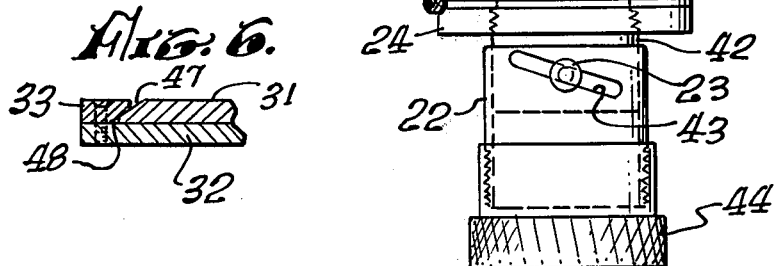
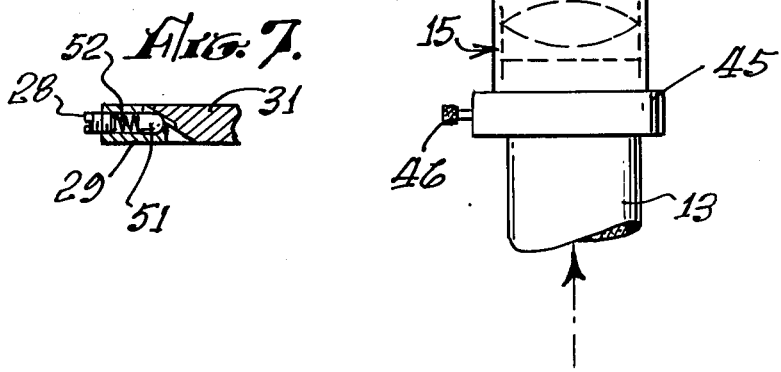

SELF DEVELOPING CAMERA FOR USE IN MACROPHOTOGRAPHY AND ENDOSCOPIC PATHOLOGY

STATEMENT OF GOVERNMENT INTEREST

The invention described herein may be manufactured and used by or for the Government of the United States of America for governmental purposes without the payment of any royalties thereon or therefor.

FIELD OF THE INVENTION

This invention pertains to the field of medicine. In particular, this invention pertains to that branch of medicine having to do with internal disorders. More specifically, the invention concerns itself with photographic observation and recording of internal body cavities. By way of further characterization, the invention pertains to an endoscopic photographic system employing self developing film plates. By way of more particular characterization, but without specific limitation thereto, this invention pertains to an endoscopic photographic system recording a plurality of images on selected areas in a single self developing photographic plate.

DESCRIPTION OF THE PRIOR ART

At the present time, there are a variety of methods and apparatus for obtaining photographic documentation of endoscopic findings. These known systems include endoscopic photographic attachments to take color transparencies using 35 millimeter medical cameras. Such cameras may employ either color negative film, color transparency film, or monochromatic film for producing black-and-white prints. While having attained a successful level of development for their intended purposes such systems suffer common drawbacks of requiring a considerable amount of time for the processing of the photographic image.

Where patients must be moved from one treatment center to another, or a rapid diagnosis is essential for effective treatment, the delays imposed by the film processing time cause the prior art system to be of limited effectiveness. As may be readily imagined, these conditions are frequently encountered in the treatment of patients within a military hospital system where the patient is commonly moved from a treatment center in a remote area to successive echelons of treatment facilities before arriving at a final treatment and, or convalescent center. Thus, it may be some time before the results of an endoscopic examination may be effectively utilized by treating physicians. Thus, a need has been long felt in the medical arts for a rapid and effective method of obtaining endoscopic photographic information.

Currently, there is no photographic system meeting the needs of this specialized demand. Limited success in this area has been achieved using a single lens type 35 millimeter camera employing a image orthicon and cathode ray tube imaging system to produce black-and-white prints on a conventional cathode ray tube, self-developing camera. Because this system is extremely expensive, and delicate to adjust and operate, it is not well suited to use in the aforedescribed military hospital systems. Similarly, another known system employs a revolving turret optical system with a self-developing camera back in one of the turret positions and other measuring equipment in other turret positions and is available for surgical amphitheatre and other large fixed endoscopic examination systems. However, this system is also very expensive and unsuited to remote field and naval vessel conditions.

SUMMARY OF THE INVENTION

The invention is directed to endoscopic photographic systems which deploy endoscopic optical examination instruments attached to be inserted within the body cavity and a light conducting fiber optic bundle which connects the endoscopic optical means to a remotely located lens and shutter arrangement. A compound mount system supports the lens and shutter system in a preselected position spaced at focal distance from a single self-developing film plate which is held in an inexpensive camera back constructed of a lightweight material such that the lens and camera assembly may be easily hand-held and adapted for portable applications. Further, a compound mount permits a plurality of endoscopic photographic images to be placed on a single film plate. This is an important feature of the system since there is less likelihood of separation of the images used for diagnosis and the patient than when individual photographic images are used. Also, a standard format may be used such that a standard of image identification may be readily implemented.

STATEMENT OF THE OBJECTS OF INVENTION

It is accordingly an object of this invention to provide an improved medical instrument.

Another object of the present invention is to provide an improved endoscopic photographic system.

A further object of this invention is to provide an endoscopic photographic system employing a self-developing camera.

Yet another object of this invention is to provide an endoscopic photographic system for producing a plurality of endoscopic images on a single photographic plate.

Yet another object of this invention is to provide an endoscopic photographic system having a selectively positioned lens mounting such that a plurality of images in a predetermined format may be obtained by successive exposures on a single photographic plate.

Other objects, advantages, and novel features of the invention will become apparent from the following detailed description of the invention, when considered in conjunction with the accompanying drawings.

BRIEF DESCRIPTION OF THE DRAWINGS

FIG. 1 is a schematic representation showing the endoscopic system of the invention in an operative environment;

FIG. 2 is an exploded view of the lens mount and focusing system of the invention;

FIG. 3 is an illustration of a single film plate showing the relative positions of a plurality of the endoscopic views obtained with the system of FIG. 1;

FIG. 4 is a front elevation of a compound lens mount illustrated in FIG. 2;

FIG. 5 is a sectional view taken along lines 5—5 of FIG. 4;

FIG. 6 is a sectional view taken along lines 6—6 of FIG. 4; and

FIG. 7 is a sectional view taken along lines 7—7 of FIG. 4.

DESCRIPTION OF THE PREFERRED EMBODIMENTS

Referring to FIG. 1, a patient 11 is illustrated with a system of the invention illustrated generally at 12 and shown in cooperative relation with respect to patient 11. As shown, a conventional endoscopic optical probe indicated at A is inserted within a body cavity of patient 11 and is connected to camera 14 via a flexible fiber optic bundle 13 which is secured in optical alignment with an objective lens assembly indicated generally at 15.

Referring to FIG. 2, the constructional details of the camera system of the invention may be more readily understood. As shown, a self-developing camera back 14 has the open-end thereof closed off by a first plate 32 upon which a first slide 31 is slidably mounted. A second slide 25 is carried on first slide 31 and supports lens and shutter assembly 15 thereon.

As illustrated, second slide 25 moves at right angles to the direction traversed by first slide 31 such that the plurality of lens positions is obtained.

Referring to FIG. 3, one arrangement showing successive photographic positions indicated at I through IX are illustrated. It will be observed that the numbering sequence is chosen such that a center row of photographic images is numbered in opposite direction from the top and bottom rows. This numbering sequence is arbitrary but the arrangement illustrated permits the minimum manipulation of the photographic equipment and, thereby, facilitates a rapid photographic recording of the desired information. In this fashion, a sequence of photographs may relate to predetermined angles and depths within the body cavity.

Referring again to FIG. 2, taken together with FIGS. 4, 5, 6, and 7, a more complete description of the compound lens mounting and focusing arrangement as used in the endoscopic system of the invention will be described. Considering first the exploded view illustrated in FIG. 2, it will be seen that first plate 32 has a system of beveled rails 33 along the lateral edges thereof and end stop pieces 34 positioned at the ends thereof. These double rails 33 provide an edge engagement with a corresponding beveled edge on plate 31 which comprises the body portion of the first slide.

This beveled engagement is illustrated at FIG. 6, in which rail 33 is shown to have a beveled edge 48 sloping inwardly to provide a retaining overhang for a corresponding beveled edge surface 47 on slide plate 31. In this fashion, plate 31 is free to slide across the surface of plate 32 to occupy selected positions within limits established by stops 34 abutting the ends of slide 31.

As shown, plate 32 has a central aperture 35 which is somewhat squared and provides an optical path from lens and shutter assembly 15 in any possible position of first and second slides 31 and 25, respectively. A detent 37 is mounted in one rail 33 and cooperates with detent notches 36 in the slide plate 31. Of course, if desired, a second detent may be provided in the other rail 33 to assist detent 37. Such a detent would cooperate with other notches, not shown, which may be spaced to alter the image spacing.

A pair of beveled rails 29 are placed on opposite sides of a central aperture 30 in slide 31. A detent 28 provides a spring biased stop to cooperate with notches along an engaged edge portion of a second slide 25.

Referring to FIG. 7, the details of this detent arrangement are illustrated. As shown, detent 28 is seen to comprise a biasing threaded plug which compresses a spring 52 urging a detent stop 51 into sectional engagement with slide 31. Of course, the detent mechanism acting between rail 33 and a first slide 31 may be constructed in a similar fashion. Similarly, other spring type detents are known in the medical instrumentation and photographic arts and choice among the various detent stop mechanisms known in these arts may be made with due consideration to the various performance trade-offs inherent in each design. Second slide 25 has upstanding boss 26 which is adapted to receive the lens and shutter assembly 15 therein. Collar 26 is provided with conventional optical engaging surfaces to support the lens and shutter assembly 15. Such a conventional means may include, for example, threads or bayonet type fittings.

Referring to FIG. 5, taken together with FIG. 2, the operational details of the focusing lens mount may be better understood. As shown, a shutter mechanism 24 is threadably received on boss 26 and, in turn, receives a similar boss 42 which extends forward of shutter 24 and receives, in a sliding fit, an outer cylinder 22 which, in turn, supports an optical lens having an aperture stop ring 44 extending outwardly therefrom. The position of cylinder 22 on cylinder 42 is therefore seen to determine the focus of the camera by adjusting the lens to film plate distance. This focusing is facilitated by means of an operating means indicated generally at 23 which extends radially outward from cylinder 42 through a spiral groove 43 such that as first cylinder 22 is rotated about cylinder 42 the operating means 23 causes cylinder 22 to be displaced axially along cylinder 42. Operating means 23 may include a threaded thumb nut arrangement which permits cylinder 22 to be secured in an adjusted position relative to cylinder 42. Once this distance is accurately determined by means of a ground glass back or other convenient focusing mechanism, little adjustment is required for a given lens and camera back arrangement. Any lens having the desired optical properties may be used in the practice of the invention. However, for purposes of completeness it should be noted that medical instrument lens of 105 millimeters focal length has proven satisfactory in developmental models.

Exposure control is performed as is conventional in endoscopic photographic arts and endoscopic optical unit A may include a light source sufficient for providing proper terminal illumination. Alternatively, fiber optic bundle 13 may include a light transmitting portion to provide illumination from an external light source to be transmitted to endoscopic optical unit A. Both arrangements are conventional in endoscopic photography and the invention may be practiced with either illumination system.

Similarly, the choice of materials for the construction of the compound mounting arrangement illustrated in FIGS. 2 and 4 as well as the focusing lens mount illustrated in FIGS. 2 and 5 may involve the selection from conventional materials. In developmental models of the invention, the lens mount and focusing arrangement employed brass and stainless steel fittings while camera back 14 was obtained from an inexpensive, fixed-focus, plastic, self-developing camera commercially available. This construction has resulted in providing a satisfactory endoscopic photographs on a variety of occasions at a cost and reliability not herebefore obtainable.

MODE OF OPERATION

Referring to FIG. 4, and FIGS. 1 and 3, the operation of the system will be described. After endoscopic photographic unit A is inserted in the patient's body cavity, the camera assembly 12 is positioned at a convenient operating position and the first slide 31 and second slide 25 are positioned in one of their extreme positions. As successive operations of the shutter 24 provide independent exposure, slide 31 is advanced to occupy the next position provided by the detent stop 36. And, similarly, a third exposure is provided by moving the slide to the next extreme position. Whereupon slide 25 is moved to its next position and the fourth exposure is then made. By the returning side 31 in this step-wise fashion to its original position with two more exposures, the central row of exposure is completed. A second indexing of the second slide 25 provides for the commencement of a third row of photographs and successive exposures accompanied by translational movements by a first slide 31 provide original line photographic images such that nine complete endoscopic images are obtained on a single self-developing film plate.

By a prearranged convention, the relationship of the photographs on the plate may correspond to predetermined locations within the body cavity, indication of progress of treatment, or other standard biomedical measuring techniques.

Of course, endoscopic optical unit A may be configured to facilitate usage in any of the endoscopic fields on examination and may include, for example, esophagascopes, gastroscopes, panendoscopes, and colonoscopes, cystoscopes, bronchoscopes, and other medical and dental applications. Additionally, the invention may be used with industrial borescopes with suitable modification.

The foregoing description taken together with the appended claims constitutes a disclosure such as to enable a person skilled in the biomedical and optical arts having the benefit of the teachings contained herein to make and use the invention. Further, the structure herein described meets the objects of invention and generally constitutes a meritorious advance in the art unobvious to such a worker not having the benefit of these teachings.

Obviously, many modifications and variations of the present invention are possible in the light of the above teachings, and, it is therefore understood that within the scope of the disclosed inventive concept, the invention may be practiced otherwise than specifically described.

What is claimed is:

1. An endoscopic photographic system for examining and recording the appearance of body cavities comprising in combination:
    endoscopic optical means for insertion at a plurality of predetermined locations within a body cavity;
    light conducting means connected to said endoscopic optical means for providing a light conducting path therefrom to the exterior of the body cavity;
    lens and shutter means attached to said light conducting means for formation and timed transmission of an optical image of the view of each predetermined location within the body cavity transmitted via said endoscopic optical means and said light conducting means;
    a camera back for positioning a single self developing film plate to receive each of said optical images formed and transmitted by said lens and shutter means; and
    movable lens mount means positioned between said lens and shutter means and said camera back for producing a plurality of photographic images on said single film plate, each of said photographic images corresponding to one of said predetermined locations within the body cavity, wherein said movable lens mount means includes:
    plate means attached to said camera back for establishing a light-tight closure therefor;
    first retaining means mounted about the peripherial edge of said plate means for providing edge retention thereon;
    an aperture centrally located in said plate means and surrounded by said first retaining means;
    movable first slide means having an aperture therein and held in sliding engagement with said plate means by cooperative edge retention by said first retaining means;
    second retaining means mounted on said first slide means and said second retaining means surrounding the aperture in said first slide means for providing edge retention thereon; and
    movable second slide means having an aperture therein and held in sliding engagement with said first slide means by cooperative edge retention by said second retaining means.

2. An endoscopic photographic system according to Claim 1 in which the aforesaid first slide means and said second slide means are arranged to move in directions mutually at right angles with respect to each other.

3. An endoscopic photographic system according to claim 1 which is adapted to be hand-held.

4. An endoscopic photographic system according to claim 1 which is adapted to form each of said photographic images according to a predetermined sequence.

5. An endoscopic photographic system according to claim 1 including:
    first detent notches carried on a marginal edge of said first slide means for indexing said first slide means;
    first detent means connected to said first retaining means and positioned to cooperate with said first detent notches to provide retention in a selected one of a plurality of positions corresponding to selected areas on the self developing film plate;
    second detent notches mounted on a marginal edge of said second slide means for indexing said second slide means; and
    second detent means connected to said second retaining means and positioned for cooperation with said second detent notches to provide retention in a selected one of a plurality of positions corresponding to selected areas on the self developing film plate.

* * * * *